(12) United States Patent
Schneider

(10) Patent No.: US 11,762,047 B2
(45) Date of Patent: Sep. 19, 2023

(54) DETERMINING A POSITION OF AN OBJECT INTRODUCED INTO A BODY

(71) Applicant: Siemens Healthcare GmbH, Erlangen (DE)

(72) Inventor: Rainer Schneider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 196 days.

(21) Appl. No.: 17/396,979

(22) Filed: Aug. 9, 2021

(65) Prior Publication Data

US 2022/0050154 A1   Feb. 17, 2022

(30) Foreign Application Priority Data

Aug. 12, 2020 (DE) .................... 10 2020 210 208.2

(51) Int. Cl.
*G01R 33/28* (2006.01)
*G01R 33/48* (2006.01)
*G01R 33/36* (2006.01)
*A61B 5/06* (2006.01)
*A61B 5/00* (2006.01)
*G01R 33/00* (2006.01)

(52) U.S. Cl.
CPC ............ *G01R 33/285* (2013.01); *A61B 5/062* (2013.01); *A61B 5/7207* (2013.01); *G01R 33/0023* (2013.01); *G01R 33/3607* (2013.01); *G01R 33/48* (2013.01); *A61B 2560/0223* (2013.01)

(58) Field of Classification Search
None
See application file for complete search history.

(56) References Cited

U.S. PATENT DOCUMENTS

| 2020/0110145 A1* | 4/2020 | Zeller ................. A61B 5/7207 |
| 2020/0166597 A1* | 5/2020 | Speier ................. H04B 13/005 |
| 2020/0396112 A1* | 12/2020 | Biber ..................... A61B 5/055 |
| 2021/0085260 A1* | 3/2021 | Schneider .......... G01R 33/5676 |
| 2021/0325525 A1* | 10/2021 | Biber ..................... G01R 33/36 |
| 2022/0057465 A1* | 2/2022 | Xie ........................ G01R 33/543 |
| 2022/0202386 A1* | 6/2022 | Leussler ................ A61B 6/527 |
| 2022/0206098 A1* | 6/2022 | Leussler ............ G01R 33/5673 |

OTHER PUBLICATIONS

Campbell-Washburn, Adrienne E., et al. "Real-time MRI guidance of cardiac interventions." Journal of Magnetic Resonance Imaging 46.4 (2017): 935-950.
German Office Action for German Application No. 10 2020 210 208.2 dated May 12, 2021.

(Continued)

*Primary Examiner* — Rodney E Fuller
(74) *Attorney, Agent, or Firm* — Lempia Summerfield Katz LLC

(57) ABSTRACT

Systems and Methods for determining a position of an object introduced into a body. An RF pilot tone is generated and is radiated into the body. Response signals modulated by the radiating into the body are received by a plurality of MRI receiver coils arranged spatially distributed outside the body and are converted into respective measurement signals. From the measurement signals, the position of the object is determined.

20 Claims, 1 Drawing Sheet

(56) References Cited

OTHER PUBLICATIONS

Hillenbrand, Claudia M., et al. "Active device tracking and high-resolution intravascular MRI using a novel catheter-based, opposed-solenoid phased array coil." Magnetic Resonance in Medicine: An Official Journal of the International Society for Magnetic Resonance in Medicine 51.4 (2004): 668-675.

Roujol S. et al.: "Advanced Passive Tracking and Visualization of MR-Compatible Diagnostic Electrophysiology Catheter.", in Proceedings of the 25th Annual Meeting of ISMRM; Honolulu, 2017; 1-3.

Schroeder, Lea, et al. "A novel method for contact-free cardiac synchronization using the pilot tone navigator." Proceedings of the 24th Annual Meeting of ISMRM, Singapore. 2016. 1-3.

Vahle, Thomas, et al. "Respiratory Motion Detection and Correction for MR Using the Pilot Tone: Applications for MR and Simultaneous PET/MR Exams." Investigative radiology 55.3 (2020): 153. pp. 1-19.

Weine J. et al.: "Interleaved White Marker Contrast with bSSFP Real-Time Imaging for Deep Learning based Needle Localization in MR-Guided Percutaneous Interventions." Proceedings of the 27th Annual Meeting of ISMRM, Montreal, 2019. 1-2.

Xu, Robert, and Graham A. Wright. "GPU accelerated dynamic respiratory motion model correction for MRI-guided cardiac interventions." Computer methods and programs in biomedicine 136 (2016): 31-43.

\* cited by examiner

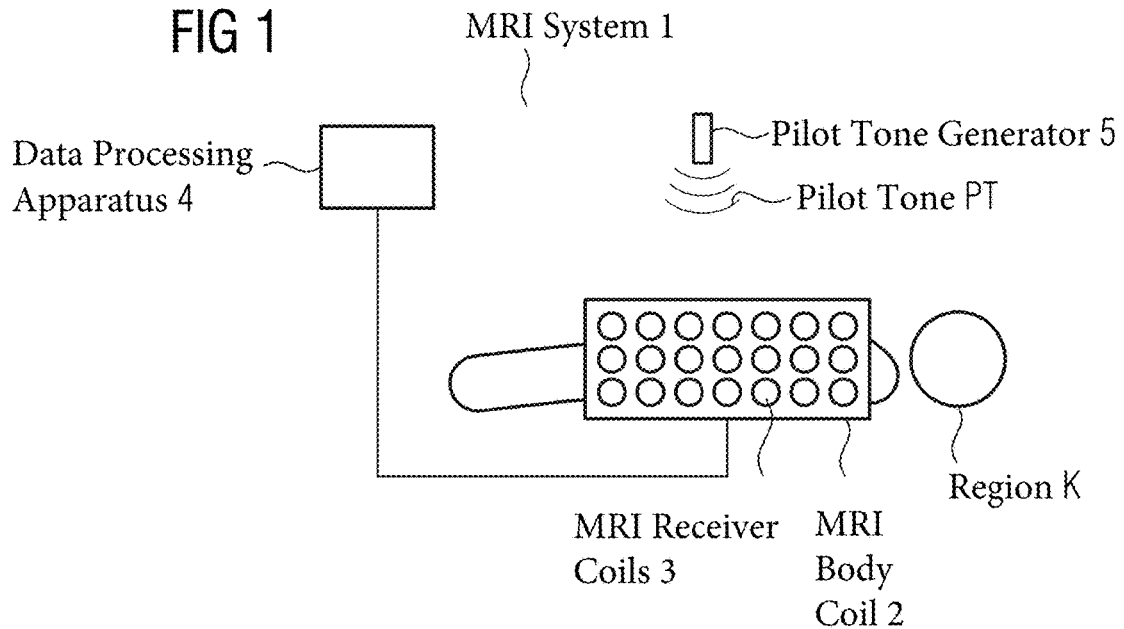
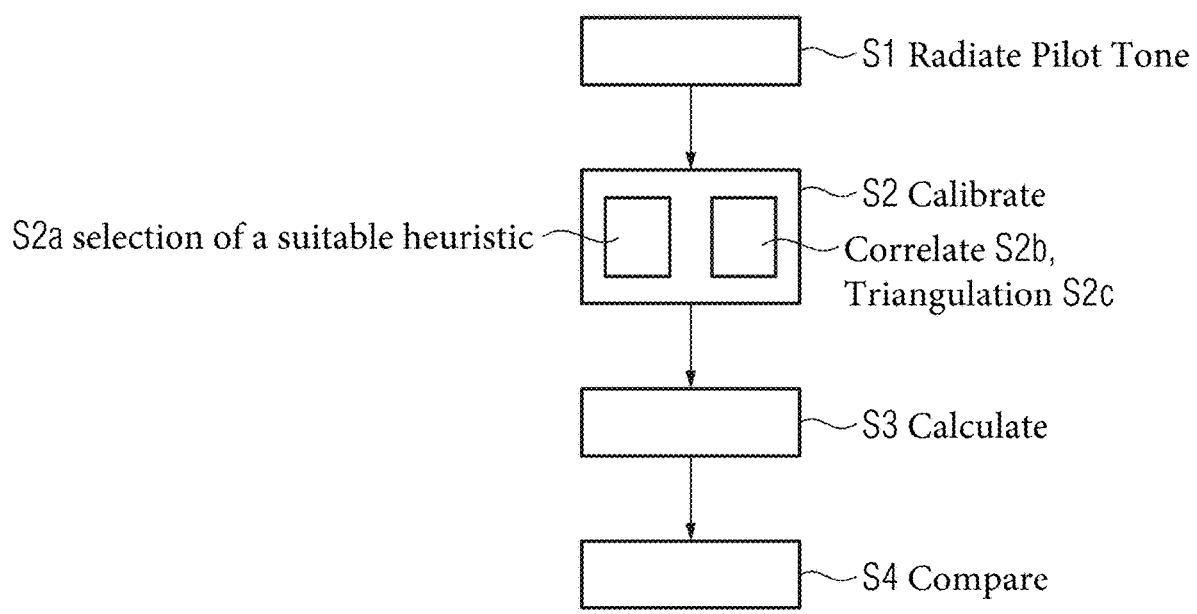

DETERMINING A POSITION OF AN OBJECT INTRODUCED INTO A BODY

CROSS REFERENCE TO RELATED APPLICATIONS

This patent document claims the benefit of DE 102020210208.2 filed on Aug. 12, 2020 which is hereby incorporated in its entirety by reference.

FIELD

Embodiments relate to a method for determining a position of an object introduced into a body and an MRI system that includes a plurality of spatially distributed MRI receiver coils, a pilot tone generator and a data processing apparatus for processing scan signals recorded by the MRI receiver coils.

BACKGROUND

In clinical healthcare, interventional magnetic resonance tomography (MRI) is of great interest, in order to enable an improved effectiveness of therapeutic interventions. Due to the absence of ionizing radiation, improved soft tissue contrast and real spatial 3D image information, it has great advantages over conventional X-ray-based fluoroscopic systems.

However, MRI also has some disadvantages in the therapeutic workflow and the MRI compatibility of devices for therapeutic intervention such as guide wires, catheters, needles, optical lightguides, probes etc. must be assured. Such devices must also be visible on MRI images that, due to the lack of protons and/or due to the non-projectional imaging of MRI, is often not the case.

The detection or making visible with MRI of devices for therapeutic intervention in interventional MRI may be achieved by passive or active tracking methods.

In the context of passive tracking methods, for example, properties of the magnetic susceptibility of the device may be used in order to emphasize signal cavities in the standard MRI imaging sequences, as described for example by Roujol, Sebastien, et al. in "Advanced Passive Tracking and Visualization of MR-Compatible Diagnostic Electrophysiology Catheter", Proceedings of the 25th Annual Meeting of ISMRM, Honolulu 2017.

Alternatively, MRI imaging sequences may be adjusted to generate a positive contrast or, a multi-off-resonance-imaging is used in order to generate a virtual image on the basis of an anatomical image and a device image. It is thereby also known to provide devices with iron markers or particles in order to emphasize this effect further. The initial identification and tracking of the devices in the body is carried out manually, that may be very difficult as soon as the device is situated outside the imaging plane. Weine, Jonathan, et al. in "Interleaved White Marker Contrast with bSSFP Real-Time Imaging for Deep Learning based Needle Localization in MR-Guided Percutaneous Interventions", Proceedings of the 27th Annual Meeting of ISMRM, Montreal 2019 describes an approach in which algorithms for artificial intelligence may improve the workflow for passive tracking.

In order to enable active tracking methods with MRI, a device for therapeutic intervention must be extended with MRI microreceiver coils and connected to the MRI system. A special MRI sequence ("MRI tracking sequence") enables the acquisition of the x, y and z-coordinates of the microcoils and thus the position of the device; see Hillenbrand, Claudia M., et al. "Active device tracking and high-resolution intravascular MRI using a novel catheter-based, opposed-solenoid phased array coil", Magnetic Resonance in Medicine: An Official Journal of the International Society for Magnetic Resonance in Medicine, 2004, 51st year, No. 4, pp. 668-675. However, such devices are rather expensive and large. Furthermore, the active MRI tracking sequence is not activated in every anatomical imaging sequence and is therefore restricted in its combination.

The pilot tone technique for identifying intrinsic body movements is described, for example, by Schroeder, Lea, et al. in "A novel method for contact-free cardiac synchronization using the pilot tone navigator", Proceedings of the 24th Annual Meeting of ISMRM, Singapore 2016. Therein, a modulated pilot tone (PT) response signal of a body is recorded via a plurality of receiver coils. Subsequently, signal shapes, signal amplitudes and specific body signal components associated with a respiratory or cardiac motion are extracted and identified by an independent component analysis. The associated signal weights and the mixing matrix may then be stored for a further data processing.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a simply implemented and reliable possibility for locating an object introduced into a body, using an MRI system.

Embodiments provide a method for determining a position of an object introduced into a body, in which:

a) a radio frequency signal ("RF pilot tone") is generated and radiated into the body, b) a response signal modulated by the radiating into the body is received by a plurality of MRI receiver coils arranged spatially distributed outside the body and is converted into respective measurement signals, and c) from the measurement signals, the position of the object is determined.

Embodiments provides a continuous location of a therapeutic device in a body without the MRI images needing to be configured for the visibility of the device therein. It is also advantageous that for location of the device, no special MRI tracking sequences are needed. In addition, the device may be located temporally in parallel with the MRI recording sequences. Furthermore, a navigator function may be implemented in a simple manner in order to configure an MRI imaging position and/or orientation.

The RF pilot tone is generated outside a frequency of an MRI pulse signal and independently thereof. The frequency lies in a region to which the MRI receiver coils are still sensitive and therefore serve as antennae for the modulated response signal. The frequency of the RF pilot tone may lie close beside the MRI frequency band, for example, at a spacing of approximately 500 kHz from it. For example, given a strength of the Bo field of 1.5 T, it may lie in a frequency range of approximately 63 MHz, for example, at 63.4429 MHz. The RF pilot tone is, for example, a monofrequency radio-frequency signal.

The RF pilot tone is radiated into the body and, for example, penetrates into the body and is modulated by the body and the object present therein. The thus modulated response signal is received by the MRI receiver coils.

The spatially distributed MRI receiver coils may be distributed, for example, matrix-like, for example, in a two-dimensional plane or—advantageously for the precise acquisition of a spatial position of the device—three-dimensionally in the space. The latter case arises, for example, in head and spine body coils.

It is a development that the device is a device for therapeutic and/or diagnostic intervention, for example, a needle, a catheter, an optical fiber cable and/or a probe. However, the object is not restricted thereto and may also be any other object that is movable in the body, specifically also for non-medical purposes. The body may be, for example, a human or animal body.

It is an embodiment for a particularly exact determination of the position of the device and for many interventional uses that the MRI receiver coils are components of at least one MRI body coil/local coil. An MRI body coil may be, for example, a head, neck, chest, spine or extremity coil or a combination thereof (e.g., a head/neck coil)

Embodiments provide where at least one MRI receiver coil includes at least one feedthrough opening for feeding the object through. This results in the advantage that a position of the device that is fed through the feedthrough opening is determinable with high accuracy directly before or during the introduction into the body. The MRI receiver coils may be configured as coils with the feedthrough opening in their center.

For the method for positional determination, before introducing the device, modulated response signals of the body without the device are recorded in order to obtain corresponding reference measurement signals (also referred to below as "body noise"). The reference measurement signals may then be calculated out from the modulated response signals together with or after the introduction of the device. This may also be designated "normalization" and improves the positional accuracy. Body noise includes modulations of the PT response signals created by the body itself that are generated, for example, by a movement of body organs, such as a respiratory or cardiac movement. The body noise may also include the effect of a presence of a hand of an operator of the device that, with manually used devices, is present in the visual field of the MRI movement coils.

This development may be implemented in an embodiment such that the steps a) to b) are first carried out without the object being situated in the body in order to obtain respective reference measurement signals in step b), and then the steps a) to c) are carried out at least once together with or after the introduction of the object into the body, wherein in step c) the position of the object is determined from normalized measurement signals that correspond to ("normalized") measurement signals cleaned of the reference measurement signals.

The normalization steps may additionally be carried out in the presence of a hand of an operator in the field of view of the MRI receiver coils.

The normalization may be implemented, for example, in that initially measurement signals of the MRI receiver coils are recorded without the presence of the device and, on the basis of the measurement signals, a signal analysis is carried out by which signal components associated with the body noise are identified and/or extracted. The analysis of the measurement signals into independent signal components may take place by typical blind source separation methods, for example, "independent component analysis" (ICA) or "principal component analysis" (PCA), etc. Therein, the measurement signals may be projected by signal analysis into subspaces, each including particular characteristic components of the measurement signals and/or measurement signal changes, e.g., respiratory or cardiac movements. The signal components may include, for example, signal weights and at least one mixing matrix.

In subsequent measurements on the basis of measurement signals of the MRI receiver coils in the presence of the device, a signal analysis may also be carried out, for example, an independent component analysis. The previously identified interference components of the body noise are removed. Since the signal analysis is a statistically independent method, it provides a very good extraction of the interference components. After removal of the interference components, the remaining signal components that now primarily represent the device may be converted back again into the space of the MRI receiver coils, in order to be further processed by data technology as normalized measurement signals.

In an embodiment, the device is moved in the body beginning from a known starting position, corresponding measurement signals are recorded during the movement, from the changes in the measurement signals, the distance covered by the device in the body is calculated and from the known starting position and the calculated distance the (current) end position of the device in the body is determined. The advantage is achieved thereby that a position of the device is also determinable further/deeper within the body with a high degree of accuracy. Herein, account is not taken of the relationship of the measurement signals of the MRI receiver coils with their known positions, but the measurement signals or changes therefrom are used directly in order to determine the device position. It is therein assumed that from the measurement signals, the movement and/or position change of the device in the body may be derived, that results, together with the known starting position, in knowledge of the end position. The recording of measurement signals and/or their changes include at least the measurement signals and/or their changes between the start and end position.

The starting position of the device on introduction into the body (also designated the "insertion position") may be determined by different methods.

In MRI receiver coils with a feedthrough opening, the insertion position results, for example, from knowledge of the position of the feedthrough opening in relation to the position of the body.

The insertion position may be acquired automatically in that at the MRI receiver coil that includes the feedthrough opening, a PT response signal is received that is far more strongly changed by the introduction of the device than with all other MRI receiver coils, for example together with the knowledge of the position of the feedthrough opening of this MRI receiver coil in relation to the position of the body. Through the introduction of the device, the MR signal is also changed, although the PT response signal permits a continuous measurement that is independent of MR encodings and MR contrasts.

Alternatively, or additionally, the determination of the insertion position of the device is also possible without the use of a feedthrough opening:

In an embodiment, the insertion position of the object on the body is determined from a correlation of the changes in the—for example normalized—measurement signals with the respective positions of the associated MRI receiver coils. This is denoted below as "triangulation". A measurement signal of an MRI receiver coil is all the more strongly changed by a PT response signal the nearer the device is situated to this MRI receiver coil (that results from the property of the device as an antenna). Through the acquisition of the absolute changes in the measurement signals of the individual MRI receiver coils in correlation with their known spatial positions, for example also to the body, the insertion position of the device on the body surface may be easily determined. This is advantageous if the MRI receiver coils are positioned in a three-dimensionally distributed arrangement since the insertion position of the device may then be determined in all three dimensions.

In order to be able to correlate the measurement signals with a distance covered by the device within the body, embodiments calibrate the measurement signals and/or their changes on the basis of measurement signals and/or changes in their previously known movements. The measurement signals are therefore calibrated in that the changes in the measurement signals are compared with changes in measurement signals that have been generated with a known movement of the device in the body. This is advantageous since the amplitude of the modulated PT response signal does not always need to be the same, even with the same boundary conditions, but due to the manner and type of the device introduced, the body region concerned, etc., may also differ for the same distance covered.

A "known distance" may be understood, for example, to be a movement of a known device of a particular kind and a particular type by a known distance (e.g., 2 cm) and possibly a known movement direction. The distance and movement direction may be determined, for example, by identification of the device in MR images. This is performed if the device is moved along an MR image recording plane. If an MR image in which the starting position of the device is determinable and an MR image in which the end position of the device is determinable are recorded, by simple measurement of the respective positions in the MR images, the physical distance covered by the device and the direction may be determined.

The calibration may be implemented, for example, so that at the start of the interventional MRI process, an initial calibration step is carried out in which the device is moved a particular distance in the body by a user or operator and the distance is correlated with the associated changes in the measurement signals. It is therefore known, following the calibration step, that changes to the measurement signals correspond to which distance covered by the device in the body.

In an embodiment, a change in the measurement signals of the MRI receiver coils during a movement of the device in the body is determined from changes in the measurement signals, by signal analysis, in particular independent component analysis, a device signal component representing the movement of the device is determined, and the device signal component is calibrated for subsequent movements on the basis of a device signal component determined from the known movement by signal analysis.

This embodiment results in the advantage that the measurement signals may be placed particularly easily in relation to a positional change of the device ("calibrated"). During movements of the device in the body subsequently to the known movement, its positional change may consequently be calculated automatically on the basis of the evaluation of the associated device signal component. A complex tracking by slice-tracking in an MR image may be dispensed with. This embodiment requires only one known starting point and subsequent positions of the device in the body may then be determined by addition of the automatically calculated position changes. In other words, it is determined at the start what size or size change in the device signal component corresponds to what actual distance covered in the body and subsequent movements may be derived therefrom. This embodiment includes, for example in a three-dimensional arrangement of the MRI receiver coils, the possibility of determining the movement or position change of the device in the body in all three spatial directions.

In an embodiment, the measurement signals or the device signal component is calibrated by at least one heuristically determined (e.g., by trial and error and/or using empirical values) parameter ("calibration factor"), for example, similarly to the known navigator function for image plane ("slice") adaptation. By the calibration factor, a distance covered by the device in the body may be associated with a device signal component and/or a change thereof corresponding to a device movement. Since different devices create a modulation of different strength in the PT response signal, the at least one heuristically determined calibration factor may be device-dependent. One development is that the at least one parameter and/or calibration factor is retrievable for a particular device from a database in which for different devices, corresponding calibration factors or similar are stored that may have been created, for example, by previously experimentally determined calibration steps.

Embodiments further provide a method for generating an MRI image by an MRI system making use of the MRI receiver coils used in the above method. In the MRI image a position, determined using the above method, of the object situated in the body is mapped.

Embodiments further provide a method for generating an MRI image by an MRI system making use of the MRI receiver coils used in the above method. A position and/or an alignment of a recording image plane tracks the object situated in the body. Thus, the advantage is achieved that the image plane in which the device introduced into the body is situated is shown to a user or operator, that facilitates a guidance of the device and a therapeutic treatment.

Embodiments further provide an MRI system including a plurality of spatially distributed MRI receiver coils and a pilot tone generator as well as a data processing apparatus for processing measurement signals recorded by the MRI receiver coils. The MRI system is configured to carry out at least one of the methods described above. The MRI system may be configured similarly to the method and produces the same advantages. Thus, the MRI system may include, for example, at least one MRI body coil that includes a plurality of spatially distributed MRI receiver coils.

BRIEF DESCRIPTION OF THE FIGURES

FIG. 1 depicts is a schematic of an MRI system according to an embodiment.

FIG. 2 depicts a possible sequence of a method for detecting a position of an object introduced into a body according to an embodiment.

DETAILED DESCRIPTION

FIG. 1 depicts a sketch of an MRI system 1 that is configured to carry out the above-described methods. The MRI system includes at least one MRI body coil 2 (provided here in the form of a body or spinal local coil) that includes a plurality of matrix-like spatially distributed MRI receiver coils 3. The MRI body coil 2 or the MRI receiver coils 3 are linked to a data processing apparatus 4 for processing measurement signals recorded by the MRI receiver coils.

The MRI system 1 is fundamentally configured to generate MRI recordings of a region of a body K surrounded by the MRI body coil 2.

A pilot tone generator 5 is provided that may be part of the MRI system 1 or a component that is independent thereof. The pilot tone generator 5 is configured and arranged to radiate radio frequency radiation (pilot tone PT) into the region of the body K surrounded by the MRI body coil 2, specifically at a frequency that lies close to the MRI pulse frequency used by the MRI system, but that is detectable by the MRI receiver coils 3. The MRI receiver coils 3 receive a response signal modulated by objects present within the field of view of the MRI receiver coils 3, the signal being in the region of the pilot tone frequency. Such objects include the body K and, if present, a hand of an operator (upper figure) and devices for therapeutic treatment such as a probe, a needle (upper figure), or suchlike. It is thereby enabled, during a therapeutic intervention, both for MRI recordings to be made and also for a position of the device in or on the body to be detected in situ. MRI pulses and the pilot tone PT may be radiated into the body simultaneously, for example, without influencing one another, since they have a sufficiently large frequency separation.

FIG. 2 depicts a possible sequence of a method for detecting a position of an object introduced into a body K for therapeutic treatment.

In a step S1 (the normalization step), a pilot tone PT is radiated into the body K without any device for therapeutic treatment being situated in the field of view of the MRI receiver coil 3. The reference measurement signals recorded therein are analyzed by signal analysis into interference components that correspond, for example, to respiratory or cardiac movements. The reference measurement signals or data derived therefrom (e.g., signal weights and mixing matrices of the interference components) are stored in a database.

In a step S2, a calibration is carried out. This may also take place by selection of a suitable heuristic, e.g., device-specific and setup-specific, calibration factor A (step S2a).

Alternatively, there may be a relation or correlation between changes to the advantageously normalized measurement signals or data derived therefrom in the event of a movement of the device within the body K between a known starting position and a known end position (step S2b). For example, known position changes $\Delta x\_kal$, $\Delta y\_kal$ and/or $\Delta z\_kal$ brought about by the movement may be assigned to corresponding signal weights $\Delta Sx\_kal$, $\Delta Sy\_kal$, $\Delta Sz\_kal$ of the device signal component calculated from the measurement signals. The signal weights $\Delta Sx\_kal$, $\Delta Sy\_kal$, $\Delta Sz\_kal$ may correspond, for example, to signal differences that represent the device in the signal patterns obtained by analysis of the signals.

For the determination of the known starting position, a triangulation of the device may be carried out (step S2c) by the MRI receiver coils 3, for example, by introducing the device through a feedthrough opening through one of the MRI receiver coils 3. The known end position may be determined, for example, on the basis of an identification of the device in an MR image or through knowledge of the movement path of the device. Alternatively, the start and end position may be determined in MR images.

In a subsequent step S3, the device is moved within the body K, starting from a known starting position and the—for example normalized—measurement signals and/or the data derived therefrom such as signal weights of a device signal component, etc., are calculated.

In a step S4, on the basis of the calibration data obtained in the calibration step S2, the measurement signal changes from step S3 are calibrated or are compared with the calibration data provided in the calibration step S2. From this, the distances $\Delta x$, $\Delta y$ and/or $\Delta z$ covered by the device in the body may then be calculated according to $$\begin{pmatrix} \Delta x \\ \Delta y \\ \Delta z \end{pmatrix} = K \cdot \begin{pmatrix} \Delta Sx \\ \Delta Sy \\ S\Delta z \end{pmatrix}$$

where K is a calibration factor matrix and $\Delta Sx$, $\Delta Sy$, $\Delta Sz$ are the signal weights determined in step S3.

If the calibration factor matrix K has been determined heuristically, for the simplest case, K corresponds to an identical scalar calibration factor A for all the dimensions. Alternatively, A is different for all the dimensions, i.e., that $$A = \begin{pmatrix} Ax & 0 & 0 \\ 0 & Ay & 0 \\ 0 & 0 & Az \end{pmatrix},$$

with the calibration factors Ax, Ay and Az determined heuristically for the respective spatial directions. If the spatial dimensional independence is absent, a heuristically determined calibration factor matrix A that also contains cross components may be accessed.

If, however, an actual movement of the device in the body has been measured during the calibration step S2, K may include the factors determined in step S3

$$K = \begin{pmatrix} \Delta x\_kal/\Delta Sx\_kal & 0 & 0 \\ 0 & \Delta y\_kal/\Delta Sy\_kal & 0 \\ 0 & 0 & \Delta z\_kal/\Delta Sz\_kal \end{pmatrix}$$

if it is assumed that the three dimensions are calculable independently of one another. If not, a matrix relationship may also be used herein with cross components.

The end position of the device results in both cases from the addition of the distances $\Delta x$, $\Delta y$ and/or $\Delta z$ covered to the starting position.

Rather than the signal weights $\Delta Sx$, $\Delta Sy$ and $\Delta Sz$, the inverse transformed measurement signal changes of the device may be used similarly.

The new position of the device may thus be represented as:

$$X\_end = K \cdot M + X\_anf \text{ where}$$

X_end: end position/new position of the device,
X_anf: starting position of the device,
M: PT-measurement signal change during the movement, for example between the starting position and the end position, and
K: calibration factor matrix, that translates the PT measurement signal change M into a position change.

If the position change is determined on the basis of a signal analysis, as described above, the following applies $$M = \Delta S = \begin{pmatrix} \Delta Sx \\ \Delta Sy \\ \Delta Sz \end{pmatrix}$$

Otherwise, M may correspond to the components of the measurement signal changes as such, wherein the entries of the calibration factor matrix may be configured accordingly.

The position determinations based upon the above embodiments may be used, for example, to move an image plane of the MRI recordings along with the position of the device so that the device and the associated body environment may be observed "in situ" by an operator.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a position of an object introduced into a body, the method comprising:
   generating and radiating a radio frequency pilot tone into the body;
   receiving response signals modulated by the radiating into the body by a plurality of MRI receiver coils arranged spatially distributed outside the body;
   converting the response signals into respective measurement signals; and
   determining from the measurement signals, the position of the object.

2. The method of claim 1, wherein the plurality of MRI receiver coils are components of at least one MRI local coil.

3. The method of claim 2, wherein the at least one MRI local coil includes at least one feedthrough opening for feeding the object through.

4. The method of claim 1, wherein generating, radiating, receiving, and converting are performed without the object being situated in the body in order to obtain reference measurement signals and then generating, radiating, receiving, converting, and determining are performed at least once together with or after an introduction of the object into the body, wherein determining the position of the object is determined from normalized measurement signals that correspond to the measurement signals cleaned of the reference measurement signals.

5. The method of claim 4, wherein generating, radiating, receiving, and converting are performed without the object being situated in the body and a signal analysis is performed based on the measurement signals in order to identify therein signal components of a body noise, and then generating, radiating, receiving, converting and determining are performed at least once together with or after the introduction of the object into the body, wherein after converting, a signal analysis is performed on the basis of associated measurement signals and from the signal components obtained, the previously identified signal components of the body noise are removed.

6. The method of claim 1, wherein the object is moved within the body starting from a known starting position, corresponding measurement signals are recorded during the movement, from changes in the measurement signals, a distance covered by the object in the body is calculated and from the known starting position and the calculated distance, an end position of the object in the body is determined.

7. The method of claim 6 wherein an initial insertion position of the object on the body is determined from a correlation of a strength of the change in the measurement signals generated in the MRI receiver coils with the respective positions of the MRI receiver coils.

8. The method of claim 1, wherein the measurement signals measured during a movement of the object within the body are calibrated based on measurement signals of previously known movements.

9. The method of claim 1, further comprising:
   determining a change in the measurement signals of the MRI receiver coils during a movement of the object in the body;
   determining from the change in the measurement signals, by signal analysis, a device signal component representing the movement of the object; and
   calibrating the device signal component for subsequent movements on the basis of a device signal component determined from the movement by signal analysis.

10. The method of claim 1, further comprising:
    determining a change in the measurement signals of the MRI receiver coils during a movement of the object in the body;
    determining from the change in the measurement signals, by signal analysis, a device signal component representing the movement of the object; and
    calibrating the device signal component based on at least one heuristically determined calibration factor.

11. The method of claim 1, wherein the object is at least one of: a needle, a catheter, a guide wire, an optical light guide, or a probe.

12. The method of claim 1, further comprising:
    generating an MRI image; and
    mapping the position of the object situated in the body in the MRI image.

13. The method of claim 1, further comprising:
    tracking the position, an alignment, or the position and the alignment of a recording image plane of the object situated in the body.

14. An MRI system for determining a position of an object introduced into a body, the MRI system comprising:
    a pilot tone generator configured to generate a radio frequency pilot tone into the body;
    a plurality of spatially distributed MRI receiver coils distributed outside the body configured to receive response signals from the radio frequency pilot tone; and
    a data processing apparatus configured to convert the response signals into respective measurement signals and determine from the measurement signals, the position of the object.

15. The MRI system of claim 14, wherein the plurality of MRI receiver coils are components of at least one MRI local coil.

16. The MRI system of claim 15, wherein the at least one MRI local coil includes at least one feedthrough opening for feeding the object through.

17. The MRI system of claim 14, wherein generating and receiving by the pilot tone generator and plurality of spatially distributed MRI receiver coils and converting by the data processing apparatus are performed without the object being situated in the body in order to obtain reference measurement signals and then generating, receiving, converting and determining are respectively performed by the pilot tone generator, the plurality of spatially distributed MRI receiver coils, and the data processing apparatus at least once together with or after an introduction of the object into the body, wherein determining the position of the object by the data processing apparatus comprises determining the position of the object from normalized measurement signals that correspond to the measurement signals cleaned of the reference measurement signals.

18. The MRI system of claim 17, wherein generating, receiving, and converting are performed without the object being situated in the body and a signal analysis is performed by the data processing apparatus on the basis of the measurement signals in order to identify therein signal components of a body noise, and then generating, receiving, converting, and determining are performed at least once together with or after the introduction of the object into the body, wherein after converting, a signal analysis is performed by the data processing apparatus on the basis of associated measurement signals and from the signal components obtained, the previously identified signal components of the body noise are removed.

19. The MRI system of claim 14, wherein the data processing apparatus is further configured to map the position of the object situated in the body.

20. The MRI system of claim 14, wherein the data processing apparatus is further configured to track the position, an alignment, or the position and the alignment of a recording image plane of the object situated in the body.

* * * * *